US008636692B2

(12) United States Patent
Roman et al.

(10) Patent No.: US 8,636,692 B2
(45) Date of Patent: Jan. 28, 2014

(54) TRANSSEPTAL SHEATH WITH AIR BUBBLE TRAP

(75) Inventors: Ricardo D. Roman, Chula Vista, CA (US); Thomas M. Castellano, Temecula, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 0 days.

(21) Appl. No.: 13/297,496

(22) Filed: Nov. 16, 2011

(65) Prior Publication Data
US 2013/0123700 A1    May 16, 2013

(51) Int. Cl.
*A61M 5/36*    (2006.01)

(52) U.S. Cl.
USPC .......................................... 604/122; 604/171

(58) Field of Classification Search
USPC ............ 604/122, 45, 164.01, 164.02, 167.01, 604/167.03, 167.06
See application file for complete search history.

(56) References Cited

U.S. PATENT DOCUMENTS

| 4,714,461 | A |   | 12/1987 | Gabel |
| 5,810,730 | A | * | 9/1998 | Swartz et al. ................. 600/434 |
| 6,186,978 | B1 |   | 2/2001 | Samson et al. |
| 6,200,315 | B1 | * | 3/2001 | Gaiser et al. ..................... 606/41 |
| 6,808,509 | B1 |   | 10/2004 | Davey |
| 6,994,687 | B1 |   | 2/2006 | Shkolnik |
| 6,997,938 | B2 |   | 2/2006 | Wang et al. |
| 2002/0198560 | A1 |   | 12/2002 | Boyle et al. |
| 2004/0147877 | A1 |   | 7/2004 | Heuser |
| 2005/0027253 | A1 | * | 2/2005 | Castellano et al. ........... 604/122 |
| 2005/0070851 | A1 | * | 3/2005 | Thompson et al. ...... 604/167.03 |
| 2005/0261636 | A1 |   | 11/2005 | Rome et al. |
| 2009/0163864 | A1 |   | 6/2009 | Breznock et al. |
| 2010/0010442 | A1 |   | 1/2010 | Shivkumar et al. |
| 2010/0218679 | A1 |   | 9/2010 | Hekmat et al. |

FOREIGN PATENT DOCUMENTS

EP    1502611 A2    2/2005

OTHER PUBLICATIONS

European Patent Office, International Search Report, Jan. 2, 2013.
European Patent Office, Written Opinion, Jan. 2, 2013.

* cited by examiner

*Primary Examiner* — Laura Bouchelle
(74) *Attorney, Agent, or Firm* — Christopher & Weisberg, P.A.

(57) ABSTRACT

A transseptal sheath defining a sheath lumen, a proximal end, and a distal end. A valve disposed within the sheath lumen proximate the distal end. The transseptal sheath defining at least one port along a portion of its periphery proximate the valve.

15 Claims, 5 Drawing Sheets

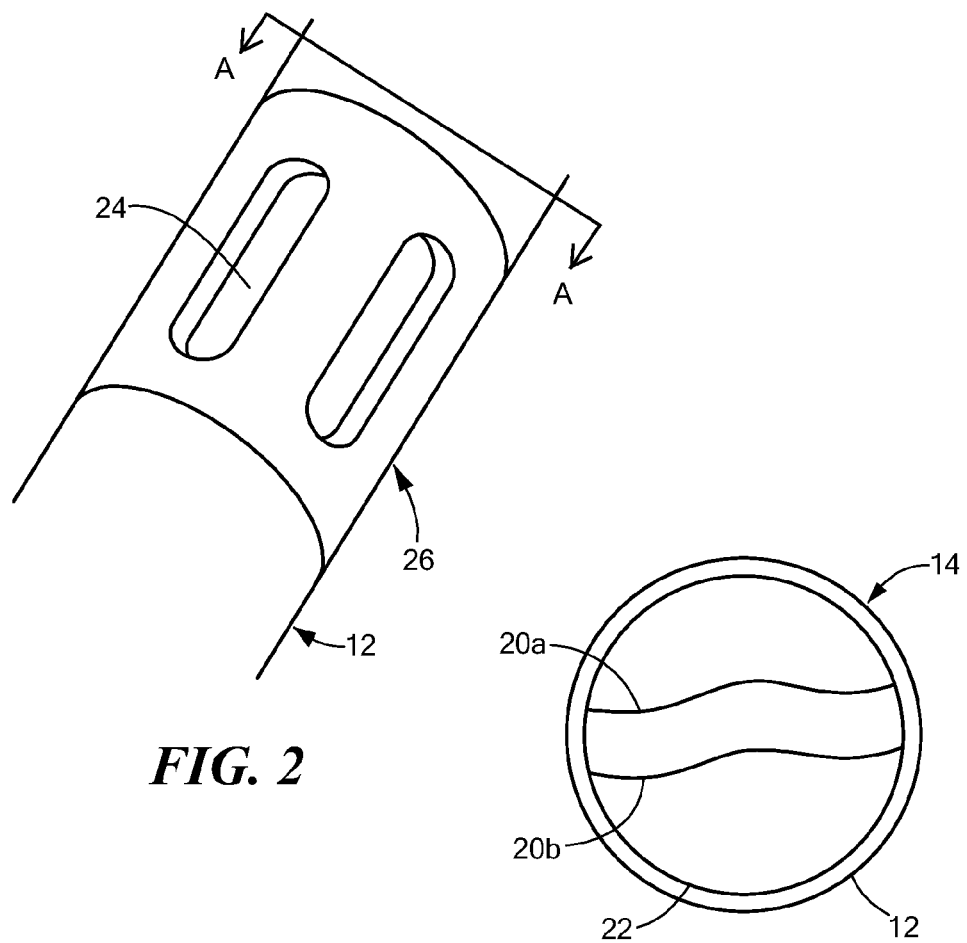
FIG. 2
FIG. 3
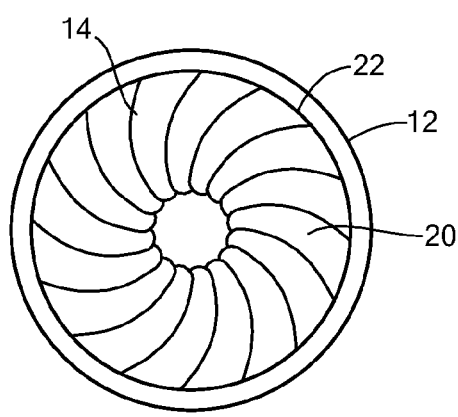
FIG. 4

TRANSSEPTAL SHEATH WITH AIR BUBBLE TRAP

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and device for purging air bubbles in a transseptal sheath away from the left atrium.

BACKGROUND OF THE INVENTION

The introduction of air bubbles into a transseptal sheath during left atrial medical treatments and procedures can be problematic. The rapid exchange of catheters and other devices into and out of the transseptal sheath may cause air to enter the sheath as bubbles or air may be present in a dissolved state within the blood itself. Such air may come out of solution under the influence of changing pressures or temperatures. The presence of air bubbles in the body, and in particular the left atrium or arterial system, may cause air embolisms, which are a well-known and potentially fatal complication that can occur in patients receiving treatments within the left atrium. Current methods and devices used to reduce the introduction of gas bubbles are targeted toward reducing the introduction of bubbles during device insertions by including an integral aspiration/flush portion and hemostatic valve on the sheath. However, even using good aspiration/flushing techniques air bubbles may still enter the sheath. Indeed, none of the current solutions contain an air bubble capture and purge system to adequately address the removal of air bubbles should they be introduced into the sheath during catheter introductions, exchanges or during aspiration/flushing operations.

Accordingly, it would be desirable to provide for air bubble capture and to purge the air bubbles away from the left atrium.

SUMMARY OF THE INVENTION

The present invention advantageously provides a method and device for purging air bubbles from a transseptal sheath prior to entering the left atrium. The medical device includes a sheath defining a sheath lumen, a proximal end, and a distal end. A valve is disposed within the sheath lumen proximate the distal end. The sheath defines at least one port along a portion of its periphery proximate the valve.

In another embodiment, the sheath is sized to receive a catheter and defines a sheath lumen, a proximal end, and a distal end. The sheath defines a chamber defining a larger cross-sectional area than a cross-sectional area of the sheath lumen. The sheath defines a plurality of ports disposed around the exterior of the chamber.

In yet another embodiment, the method includes providing a transseptal sheath defining a proximal end and a distal end having a distal tip. The sheath defines a sheath lumen and at least one port on its exterior proximate. The distal tip is positioned within the left atrium of the heart. A secondary medical device is slideably inserted within the sheath lumen. Air bubbles are released from the sheath lumen out through the plurality of ports into the right atrium.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a front cross-sectional view of the elongate transseptal sheath shown in FIG. 1 showing a plurality of ports;

FIG. 3 is front cross-sectional view through section A-A of FIG. 2 showing the secondary valve;

FIG. 4 is a front cross-sectional view of another embodiment of the second valve shown in FIG. 1;

DETAILED DESCRIPTION OF THE INVENTION

Figure 1:
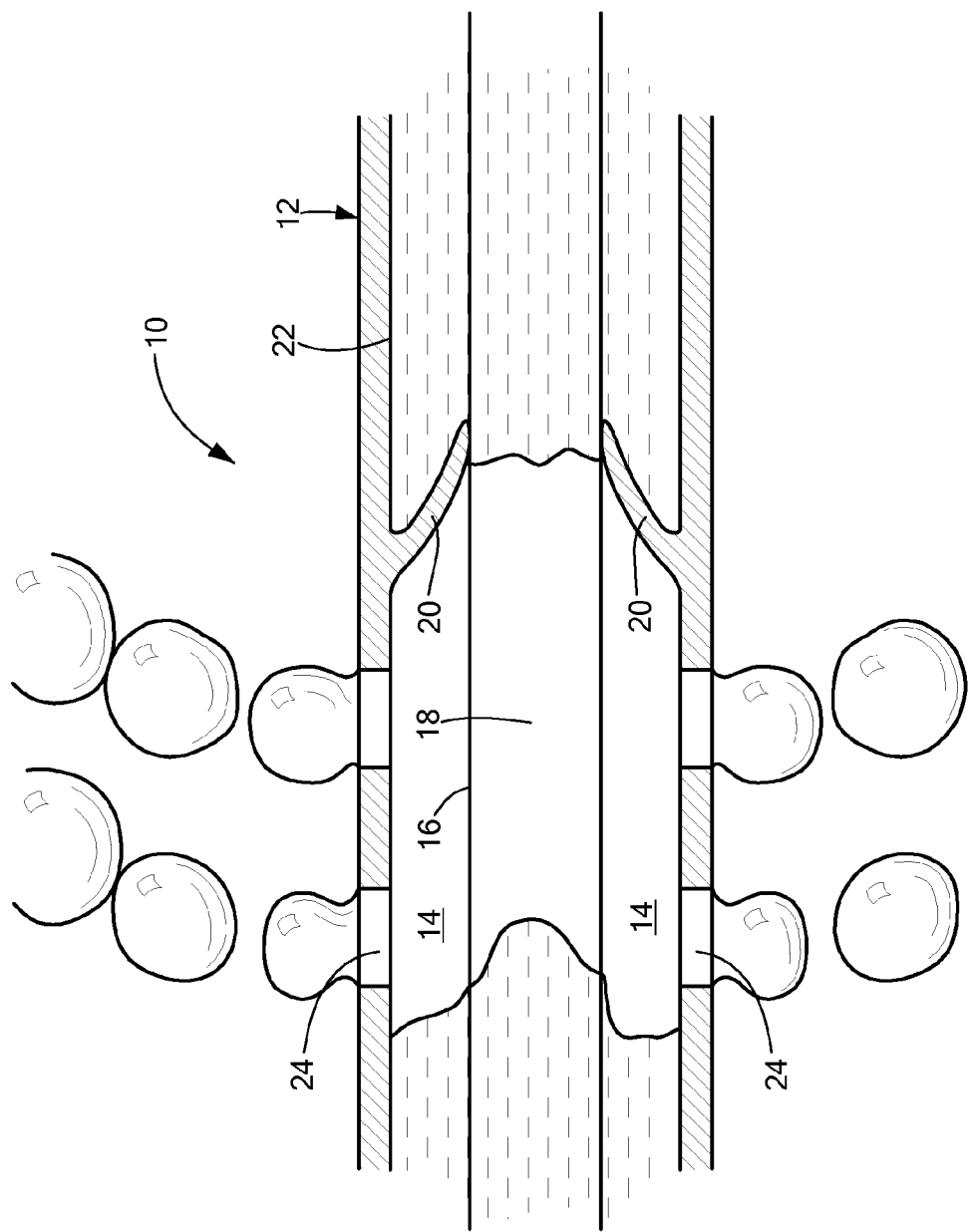
FIG. 1 is a side cross-sectional view of an exemplary transseptal sheath constructed in accordance with the principles of the present invention.

Now referring to the drawings in which like reference designators refer to like elements, there is shown in FIG. 1 an exemplary air bubble capture and purge transseptal sheath constructed in accordance with the principles of the present invention and designated generally as "10." The transseptal sheath 10 may include an elongate sheath 12 sized to be insertable within a portion of the body with the distal tip placed within the left atrium. The sheath 12 may be composed of biocompatible materials, for example, nylon, polyurethane, polyethylene and the like, and may be highly flexible as to be steerable and movable within the vasculature and heart chambers. The sheath 12 may include a proximal end, defined as a portion of the sheath 12 positioned toward an incision or entry point to a patient, and a distal end positioned toward a target treatment region within, for example, the left atrium.

The sheath 12 may further define a sheath lumen 14 through which a secondary medical device 16 may be slideably inserted during a medical procedure. The sheath lumen 14 may define a diameter larger than the diameter of the secondary medical device 16 to be inserted within the sheath lumen 12. In particular, the inner diameter of the sheath lumen 14 may be slightly larger than the outer diameter of the secondary medical device 16 such that the secondary device 16 is substantially friction fit with an interior wall 22 of the secondary medical device 16 when slid through the sheath lumen 14. The secondary medical device 16 may be an endovascular catheter or any other diagnostic or therapeutic device sized to be received within the sheath lumen 14, for example, an RF, microwave, cryogenic, or electroporation treatment device having a treatment region at its distal end or diagnostic device may be received within sheath 12. In a particular configuration, the secondary medical device 16 is a cryogenic or RF ablation device having an elongate catheter shaft 16 disposable within the sheath lumen 14 and having an ablation tip. The secondary medical device 16 may define a secondary medical device lumen 18 operable to transport volatile fluids, for example, cryogenic fluids, and/or receive a guidewire. Accordingly, in a configuration, the secondary medical device lumen 18 may be substantially fluidly isolated from the sheath lumen 14 such that violate fluids do not leak or otherwise perfuse into the sheath lumen 14. Optionally, a contrast medium, for example, a florescent dye, may be circulated through either the secondary medical device lumen 18 or the sheath lumen 14 and out through the distal end of the sheath 12. The contrast medium may be operate to indentify structures proximate the distal end of the sheath 12, for example, the pulmonary veins and the left atrial appendage.

The transseptal sheath 12 may further include at least one valve, for example, at least one flaps 20 disposed within the sheath lumen 14 and extending from the interior wall 22 of the sheath 12. For example, the flaps 20 co-operate as a valve to control or trap the air bubbles within the sheath lumen 14. The flaps 20 may be composed of the same or similar materials to that of the sheath 12. For example, the flaps 20 may be highly flexible and composed of a biocompatible material, for example, nylon, polyurethane, polyethylene and the like. Alternatively, the flap 20 may be a membrane substantially impermeable to air bubbles and occluding a substantial portion of the sheath lumen 14. In an exemplary configuration, the flaps 20 may be circumferentially disposed around the interior wall 22 and extend a distance away from the interior wall such that the sheath lumen 14 is substantially or entirely occluded by the flaps 20. In particular, each flap 20 may be spaced a distance from an adjacent flap 20, either radially or longitudinally, along a portion of the sheath 16, or may abut an adjacent flap 20.

In the configuration shown in FIG. 1, flaps 20 are shown extending from opposite positions on the interior wall 22. Each flap 20 may further be biased in a particular orientation and direction. For example, the flaps 20 may be biased to lay in a position substantially orthogonal to the inner wall 18. When a force is applied to the flaps 20, the flaps 20 may flex to allow the secondary medical device 16 to be guided through the sheath lumen 14. When flexed, the flaps 20 apply a force on the secondary medical device 16 such that at least a substantially fluid tight seal is formed between the secondary medical device 16 and the flaps 20. For example, as shown in FIG. 1, the secondary medical device 16 may push the flaps 20 into a flexed state when slideably inserted within the sheath lumen 14. The force applied by the flaps 20 back onto the secondary medical device 16 operates to help prevent air bubbles from flowing from a position proximal the flaps 20 to a position distal the flaps 20. In particular, air bubbles or other gasses trapped in the sheath lumen 14 in between the secondary medical device 16 and the interior wall 22 are at least substantially impeded by the flaps 20 when in contact with the secondary medical device 16. Such gasses thus remain in the sheath lumen 14 at a position proximal the flaps 20 as the secondary medical device 16 is advanced toward the distal end of the sheath 12. Alternatively, the flaps 20 may define a self-adjusting aperture, sized to receive the secondary medical device 16 such that when the secondary medical device traverses the aperture, any air bubbles may be isolated on the proximal side of the flaps 20.

Disposed proximal the flaps 20 are a plurality of air bubble ports 24 defined by the sheath 12. In particular, the sheath 12 may define air bubble ports 24 in fluid communication with the sheath lumen 14 and the exterior of the device 10. For example, as shown in FIG. 1, two pairs of ports 24 are defined on a portion of the sheath 12 proximal the flaps 20. The ports 24 are operable to passively purge air bubbles trapped by the flaps 20 from the sheath lumen 14, or during flushing which provides a pressure gradient between the fluid and air bubbles inside the sheath lumen 14 and fluid outside the sheath 12, i.e., the pressure inside the sheath lumen 14 is greater than the pressure outside the sheath 12 causing air bubbles or gasses to flow out of the transseptal sheath lumen 12. The pressure gradient may also be created, for example, by the insertion of the secondary medical device 16 into the sheath lumen 14, which displaces a portion of the blood flowing within the sheath lumen 14 following insertion into the body. Air bubbles, or other gasses, that enter the sheath lumen 14 from the proximal end of the device 10, may flow toward the distal end of the device where the pressure may be lower owing to, for example, an opening in the sheath 12 that facilitates the navigation of the secondary medical device 16 out of the sheath 12 toward a target region. As the air bubbles flow toward the distal end of the sheath 12 they will encounter the flaps 20 and be purged out through the ports 24 into the right atrium Now referring to FIG. 2, the air bubble ports 24 may define any shape or size and may be defined at a location that will be located within the right atrium when the distal tip is located within the left atrium. For example, each port 24 may be spaced a distance apart from an adjacent port 24 and be substantially elongate in shape and may define a diameter, for example, of approximately 1 micron to approximately 0.3 mm. The spacing of the ports 24 may also be fabricated such that the kink radius of the sheath 12 may substantially unaffected by the inclusion of the ports 24. In a configuration, the ports 24 may circumferentially disposed about the exterior of the sheath 12 such that air bubbles located about any portion of the secondary medical device 16 may be purged from the sheath lumen 14.

Optionally, the sheath 12 may further include a collar or coupler 26 that defines the ports 24 and which may be composed of the same material, or substantially the same material, as the sheath 12, or other biocompatible materials such as titanium or other metals. The collar 26 may be rotatably coupled to and contiguous with the sheath 12 such that the connection between the sheath 12 and the collar 26 is fluidly tight. The collar 26 may rotate about the sheath 12 such that the direction at which the air bubbles are purged can be adjusted. For example, the collar 26 may include ports 24 along a single side of the sheath 12. Accordingly, the collar may be rotated prior to inserting into the device 10 into the body to enhance the purging of air bubbles by directing the ports 24 vertically as the air bubbles rise. The collar 26 may alternatively be integrated and with the sheath 12 and may include a radiopaque marker (not shown) such that the collar 26 may be visible with fluoroscopy or with other imaging devices such that the position of the ports 24 may be identified during a procedure. For example, when the distal tip of the sheath 12 is inserted within the left atrium, the physician may identify the position of the ports 24 before inserting the secondary medical device 16 within the sheath lumen 14 to ensure air bubbles are purged into the right atrium.

Alternatively, the collar 26 may be disposed around the outer diameter of the sheath 12 and be sized to seal the ports 24 during certain applications. For example, the collar 26 may be slideably movable along the major axis defining by the sheath 12 and around the outer diameter of the sheath 12 to seal the ports 24 during, for example, the transport of a contrast medium through the sheath lumen 14 toward the distal end. Sealing the ports 24 during transport of the contrast medium prevents the contrast medium from egresses out of the sheath 12 through ports 24. After the contrast medium has been delivered to the target treatment site, the collar 26 may be slid away from the ports 24 such that they are in fluid communication with the exterior environment.

Now referring to FIG. 3, in another configuration, the flaps 20 be affixed to a single side of the interior wall 22 and may extend along at least substantially the entire diameter defined by the inner wall 22. For example, each flap 20 may define an elasticity and rigidity such that it operates substantially as a flexible cantilever. In an exemplary configuration, a first flap 20*a* is positioned proximal and affixed to an opposite side of the inner wall 22 in reference to a second flap 20*b*, each flap 20 extending substantially the entire diameter of the sheath lumen 14. When the secondary medical device 16 is inserted within the sheath lumen 14, and slideably guided passed the first flap 20*a* and the second flap 20*b*, the first flap 20*a* flexes and contacts a first side of the secondary medical device 16, and the second flap 20*b* flexes and contacts a second side of the secondary medical device 16. Flaps 20*a* and 20*b* may further be sized and dimensioned to at least substantially occlude fluid flow within the sheath lumen 14 when flexed and contacting the secondary medical device 16 such that air bubbles may be trapped proximate the flaps 20*a* and 20*b* and purged out through ports 24.

Now referring to FIG. 4, in another configuration, the flaps 20 may define substantially leaf-like petal structures that circumferentially surround a portion of the sheath lumen 14. In particular, each flap 20 may affixed at a first end to a portion of the interior wall 22 while a second end may extend toward the center of the sheath lumen 14. Each adjacent flap 20 may at least partially overlap an adjacent flap 20, which may further enhance stopping the air bubbles from passing the ports when the secondary medical device 16 when it is slid through the sheath lumen 14. Further, the flaps 20 may extend from the interior wall 22 to a position proximate the center of the sheath lumen 14 such that the secondary medical device 16 may slide into and out of the sheath lumen 14 with limited friction from the flaps 20 and may create a substantially fluid-tight seal with the secondary medical device 16.

Figure 5:
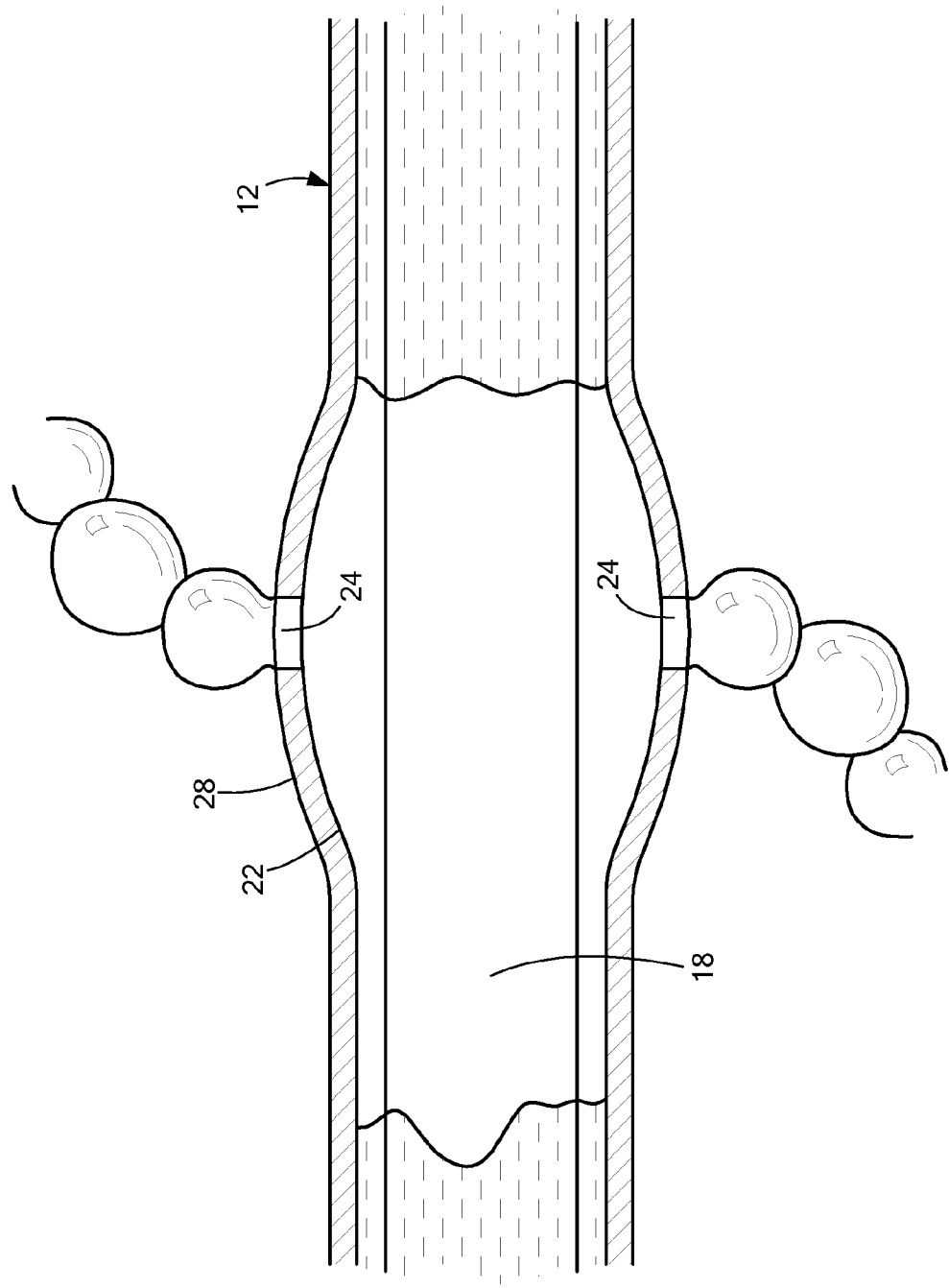
FIG. 5 is a side cross-sectional view of another secondary valve constructed in accordance with the principles of the present invention.
Figure 6:
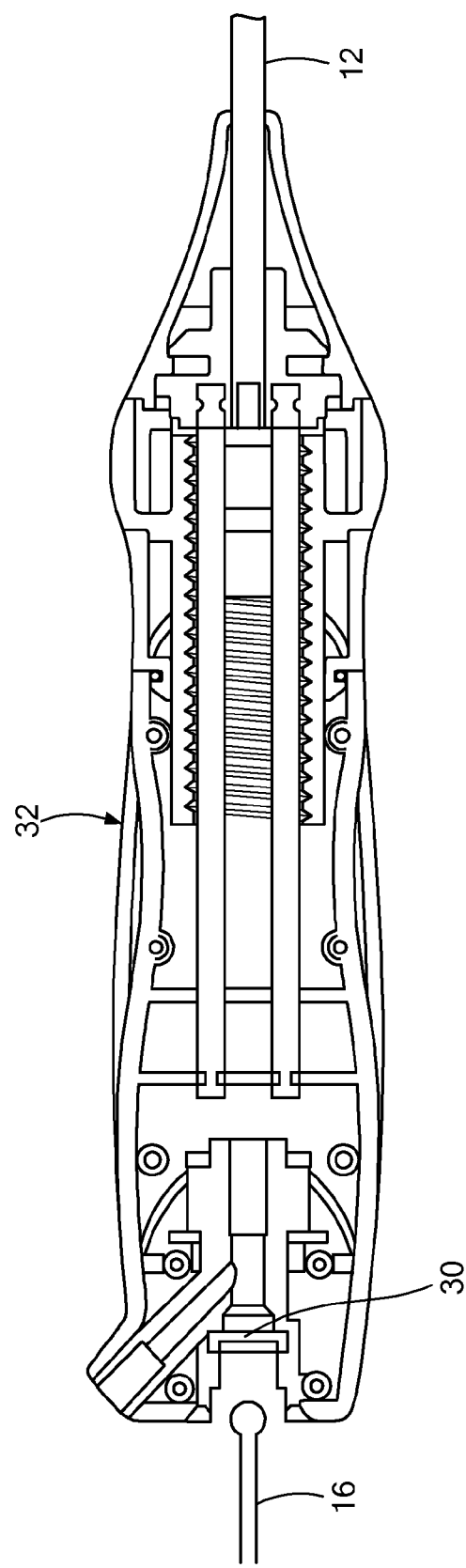
FIG. 6 is a side cross-sectional view of a transseptal sheath showing the proximate hemostasis valve and aspiration/flush port constructed in accordance with the principles of the present invention.

Now referring to FIG. 5, in another configuration, a proximal portion of the sheath 12 may define a chamber 28 sized to trap air bubbles moving to the distal end within the sheath lumen 14. The chamber 28 may define a larger cross-sectional area compared to the distal portion of the sheath 12. In particular, the chamber 28 may define a larger volume than sections of the sheath 12 disposed on opposite sides of the chamber 28. The larger volume of the chamber 28 allows for a larger volume of space for any trapped air bubbles and other fluids such as blood to occupy prior to purging. For example, because the secondary medical 16 may be friction fit with the interior wall 22 when slid within the sheath lumen 14, any air bubbles present within the sheath lumen 14 may be substantially compressed within the narrow gap between the inner wall 22 and the outer wall of the secondary medical device 16. As the air bubbles emerge into the chamber 28, they may expand owing to the decrease in pressure and larger area and become too large to re-enter the narrow gap on the opposite side of the camber 28 and are thus trapped within the chamber 28. The air bubbles may then rise toward the ports 24 where they are purged. It is further contemplated that optionally any configuration of the flaps 20 may be included just distal to the chamber 28 and operates to trap the air bubbles within the chamber 28.

Positioned at the proximal end of the transseptal sheath is an introducer valve 30, for example a hemostasis valve, operable to prevent air from entering the sheath 12 when the secondary medical device 16 is inserted within the transseptal sheath 12. The introducer valve 30 may be composed of flexible material and form a substantially fluid tight seal with the secondary medical device 16 when inserted into the transseptal sheath 12. Accordingly, the device 10 may provide for at least two valves: the flaps 20 and the introducer valve 30 to prevent air bubbles from traversing the sheath lumen 14 toward the distal end of the sheath 12. The device 10 may further be coupled to a handle 32 in which the introducer valve 30 may be disposed. It is contemplated any of the above components and features of the device 10 described above may be used with any embodiment of the device 10 discussed herein.

Figure 7:
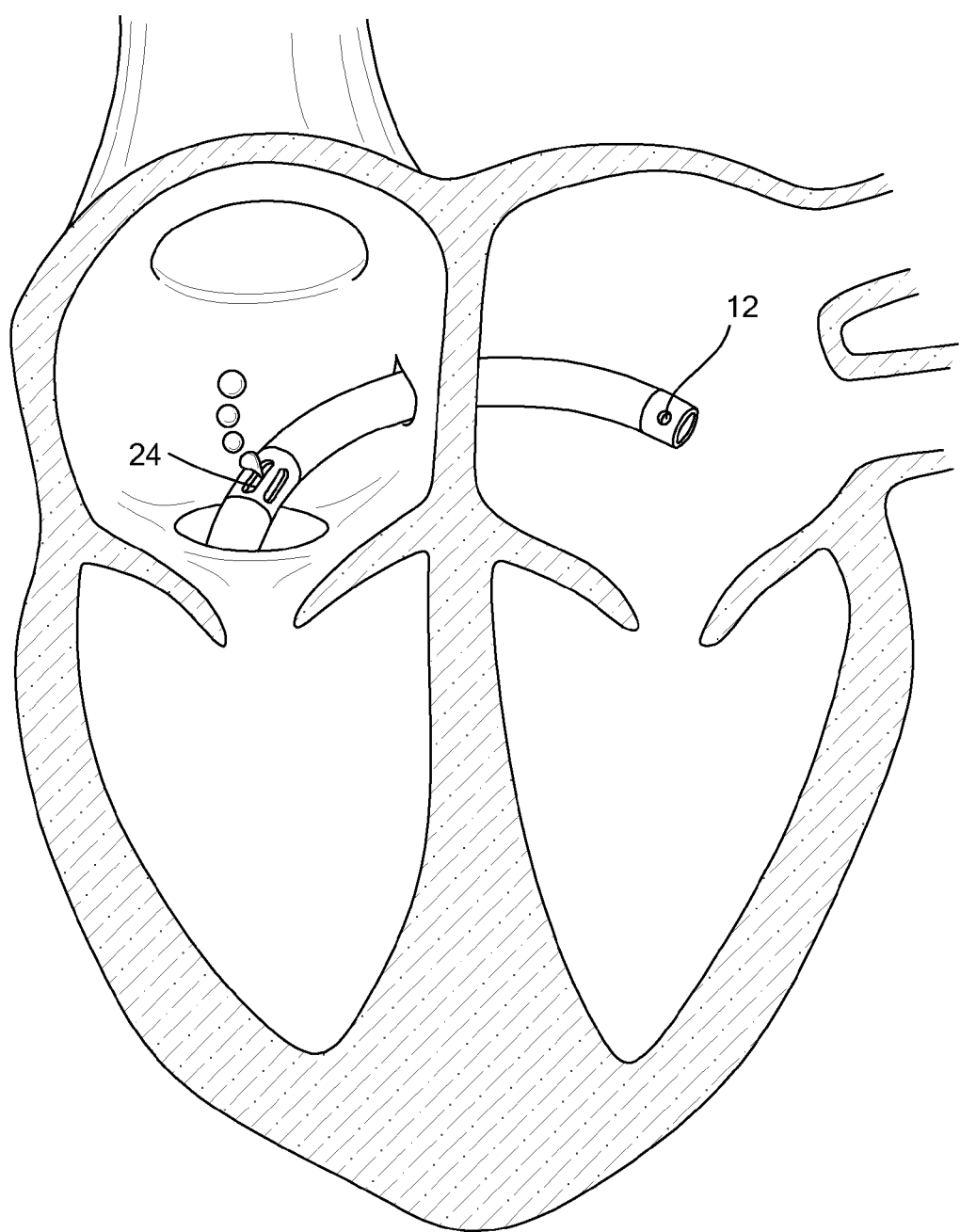
FIG. 7 is a front cross-sectional view of the heart showing the transseptal sheath of FIG. 1 within the heart releasing bubbles into the right atrium while the distal tip is within the left atrium.

Now referring to FIG. 7, in an exemplary method of use, a subcutaneous incision or a surgical incision, for example a sub-xyphoid incision, may be made on the body of the patient for insertion of the transseptal sheath 12. The sheath 12 may be guided into position toward a target treatment region, for example, the left atrium. For example, the sheath 12 may be guided through right atrium and transseptally into the left atrium for a desired procedure to be performed, for example, cardiac ablation to correct atrial fibrillation. The secondary medical device 16 may be slideably inserted through the hemostasis valve 32 into the transseptal sheath. The secondary medical device 16 may be guided through the sheath lumen 14 toward the target treatment region. As the secondary medical device is navigated toward the distal end of the sheath 12, the secondary medical device 16 may contact and form at least a substantially fluid tight seal with the flaps 20 and/or chamber 28. Any air bubbles that enter or are formed within the sheath lumen 14 proximal the flaps 20 or chamber 28, may be trapped. The trapped air may be purged out through the ports 24, which may be positioned, for example, in the right atrium.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device positionable within a patient's heart, the medical device comprising:
    a sheath sized to receive a catheter, the sheath defining a sheath lumen, a proximal end, a distal end, and a distal tip;
    the sheath defining a chamber, the chamber defining a larger cross-sectional area than a cross-sectional area of the sheath lumen;
    a valve disposed within the sheath lumen proximate the distal end; and
    the sheath defining a plurality of ports disposed around the exterior of the chamber proximal the valve, the plurality of ports and the valve being a distance from the distal tip of the sheath such that when the distal tip of the sheath is positioned in a left atrium of the heart, the plurality of ports and the valve are positioned within the right atrium of the heart.

2. The medical device of claim 1, further including a secondary medical device receivable within the sheath lumen.

3. The medical device of claim 2, wherein the valve includes a plurality of flaps circumferentially disposed about the sheath lumen within the sheath.

4. The medical device of claim 3, wherein the plurality of flaps impedes the passage of air bubbles when the secondary medical device traverses a portion of the plurality of flaps.

5. The medical device of claim 3, wherein at least a portion of a first flap of the plurality of flaps overlaps at least a portion of a second flap of the plurality of flaps.

6. The medical device of claim 2, wherein the secondary medical device defines a secondary medical device lumen, and wherein the secondary medical device lumen is isolated from the sheath lumen.

7. The medical device of claim 1, wherein the plurality of ports is temporarily sealable during a medical procedure.

8. The medical device of claim 1, further including a collar integrated with a portion of the sheath, and where in the collar defines the plurality of ports.

9. The medical device of claim 8, wherein the collar is composed of materials visible under fluoroscopy.

10. The medical device of claim 1, wherein the catheter is substantially friction fit within the sheath lumen.

11. The medical device of claim 1, further comprising a handle coupled to the sheath.

12. The medical device of claim 11, further comprising a hemostatic valve coupled to the handle.

13. The medical device of claim 12, wherein the catheter is slideably received within a portion of the handle.

14. The medical device of claim 1, wherein the catheter defines a lumen, and wherein the catheter lumen is substantially isolated from the sheath lumen.

15. The medical device of claim 13, further including a first fluid pressure within the sheath and a second fluid pressure within the chamber, and wherein the first fluid pressure is greater than the second fluid pressure.

* * * * *